Figure 1:
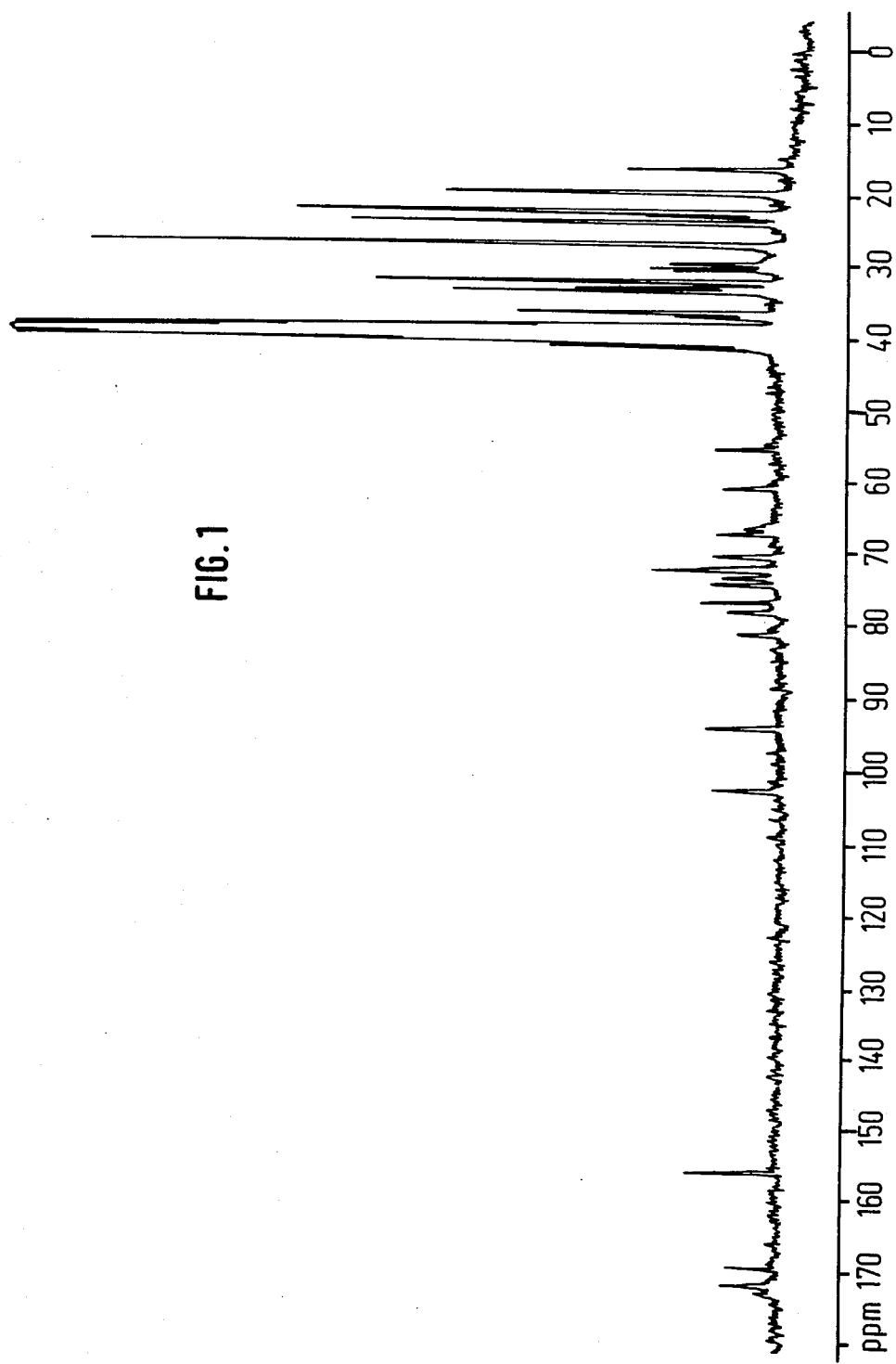

United States Patent [19]

Welzel et al.

[11] Patent Number: 4,684,626

[45] Date of Patent: Aug. 4, 1987

[54] MOENOMYCIN A DERIVATIVES AND THEIR USE AS ANTIBIOTICS

[75] Inventors: Peter Welzel; Franz Kunisch, both of Bochum; Hermann Stein, Gladbeck; Aranka Hiltmann née Ponty; Frithjof Kruggel, both of Bochum, all of Fed. Rep. of Germany

[73] Assignee: Hoechst Aktiengesellschaft, Fed. Rep. of Germany

[21] Appl. No.: 611,567

[22] Filed: May 18, 1984

[30] Foreign Application Priority Data

May 21, 1983 [DE] Fed. Rep. of Germany ....... 3318594

[51] Int. Cl.$^4$ .................. A61K 31/71; C07H 15/04
[52] U.S. Cl. .................... 514/25; 536/16.8; 536/17.2; 536/117; 514/53
[58] Field of Search ............ 536/16.8, 16.9, 17.2; 424/180, 181; 514/25, 20, 53

[56] References Cited

U.S. PATENT DOCUMENTS 3,432,597  3/1969  Schacht et al. .............. 424/118
4,362,866 12/1982  Igarashi et al. ............. 536/16.8

FOREIGN PATENT DOCUMENTS

P3221732 12/1983 Fed. Rep. of Germany .

OTHER PUBLICATIONS

Welzel et al., Carbohydrate Research, 126 (1984) C1–C5.
Welzel et al., Tetrahydron, vol. 39, No. 9, pp. 1583–1591, (1983).

*Primary Examiner*—Johnnie R. Brown
*Assistant Examiner*—Elli Peselev
*Attorney, Agent, or Firm*—Finnegan, Henderson, Farabow, Garrett & Dunner

[57] ABSTRACT

Compounds

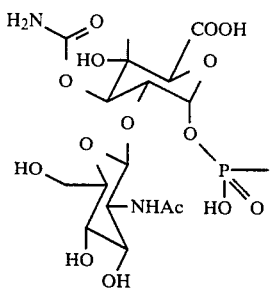

(9)

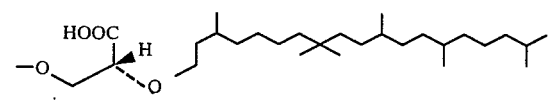

and

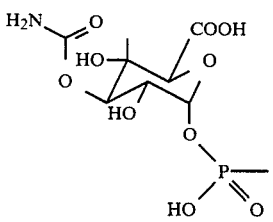

(10)

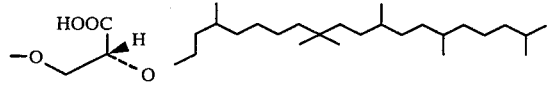

have valuable antibiotic activity. A method of treating microbial diseases using them is described as well.

4 Claims, 2 Drawing Figures

MOENOMYCIN A DERIVATIVES AND THEIR USE AS ANTIBIOTICS

According to U.S. Pat. No. 3,432,597, catalytic hydrogenation of moenomycin A of structure 1 (Angewandte Chemie 93, 130, 1981) results in decahydromoenomycin A of formula 2 which, according to German Patent Application No. P 32 21 732.3 (HOE 82/F 122), is converted to ozonization, with elimination of the chromophor unit A, into the compound 3, which has antibiotic activity and which still contains the sugar units D-galacturonic acid (B), N-acetyl-D-glucosamine (E), D-glucose (D), N-acetyl-D-quinovosamine (C) and moenuronic acid (F) which were originally contained in the moenomycin.

It is described, in German Patent Application No. P 33 01 430.2 (HOE 83/F 006), that successive elimination of the sugar units D and B from compound 3 also leads to new compounds (7 and 8) having antibiotic activity. To eliminate the sugar unit D-glucose (D) from 3, first the dibenzylidene derivative 5 is prepared, by reaction of 3 with benzaldehyde in the presence of anhydrous zinc chloride, and then the monobenzylidene derivative 6 is prepared from this using NaIO₄ in acetic acid, with elimination of D, and 6 is converted by catalytic hydrogenation, advantageously with palladium/charcoal, with elimination of the benzyl radical, into the compound 7 which contains no glucose. Subsequent elimination of the sugar unit D-galacturonic acid (B) from 7 is carried out in an analogous manner in acetic acid, and 8 is obtained.

It has now been found, surprisingly, that further elimination of the sugar unit N-acetyl-D-quinovosamine (C) from 8 using NaIO₄ in acetic acid, with the formation of 9, and the subsequent elimination of the sugar unit N-acetyl-D-glucosamine (E), with the formation of 10, also leads to new compounds (9 and 10) having antibiotic activity.

Thus the invention relates to a compound of the formula 9

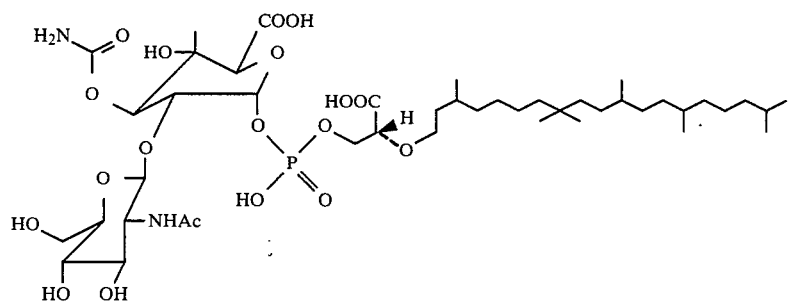

and a compound of the formula 10

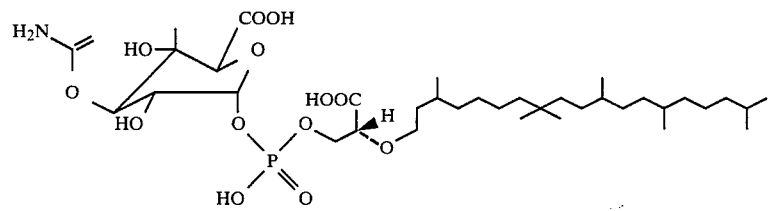

The invention also relates to a process for the preparation of the compound of the formula 9, which comprises subjecting a compound of the formula 8

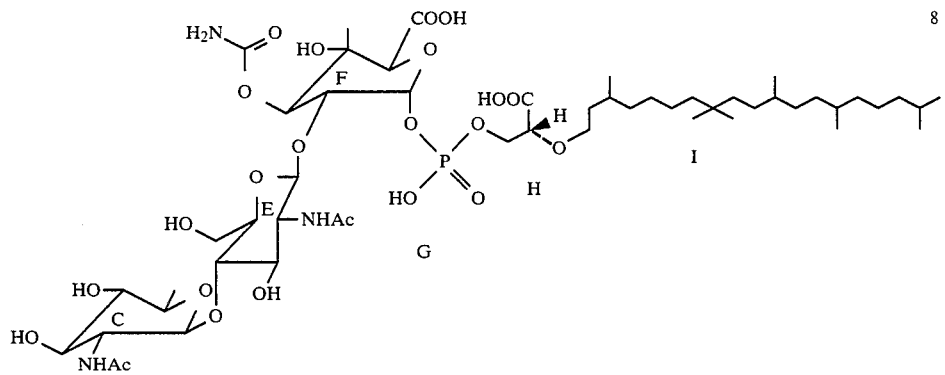

to cleavage with NaIO₄.

The invention also relates to a process for the preparation of the compound 10, which comprises subjecting a compound of the formula 9 to cleavage with NaIO₄.

The invention also relates to the use of the compound of the formula 9 as an antibiotic and to the use of the compound of the formula 10 as an antibiotic.

The reaction sequences are illustrated by the diagram below:

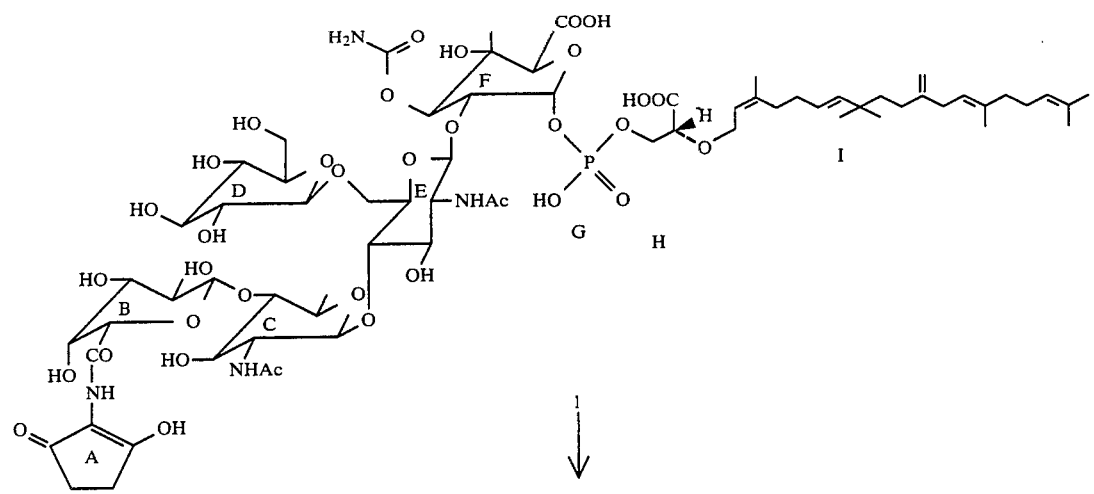
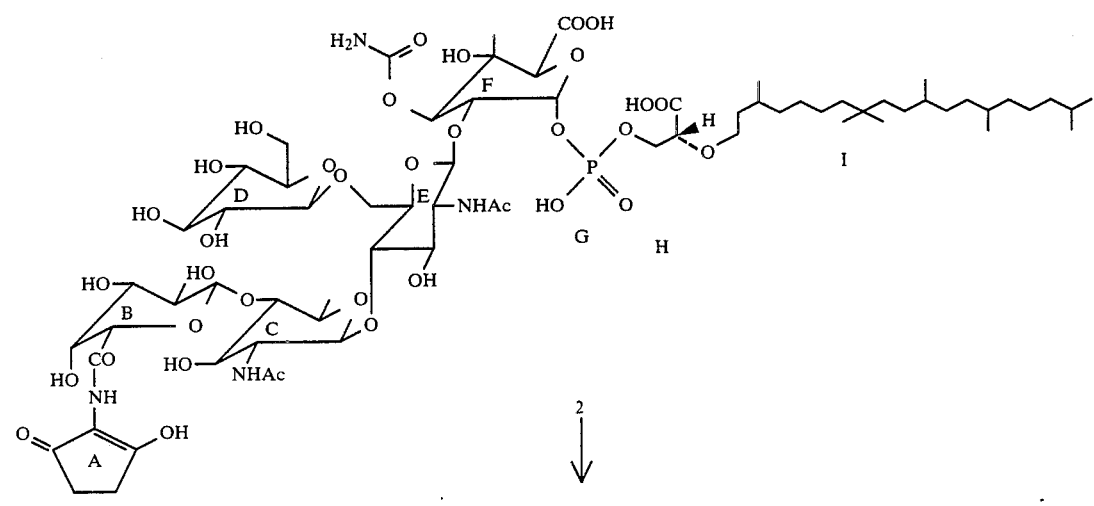
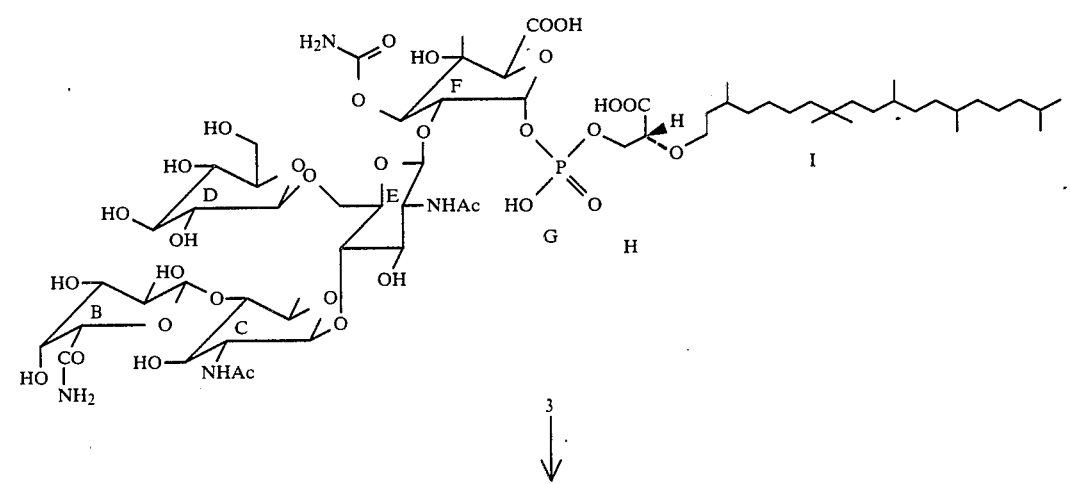

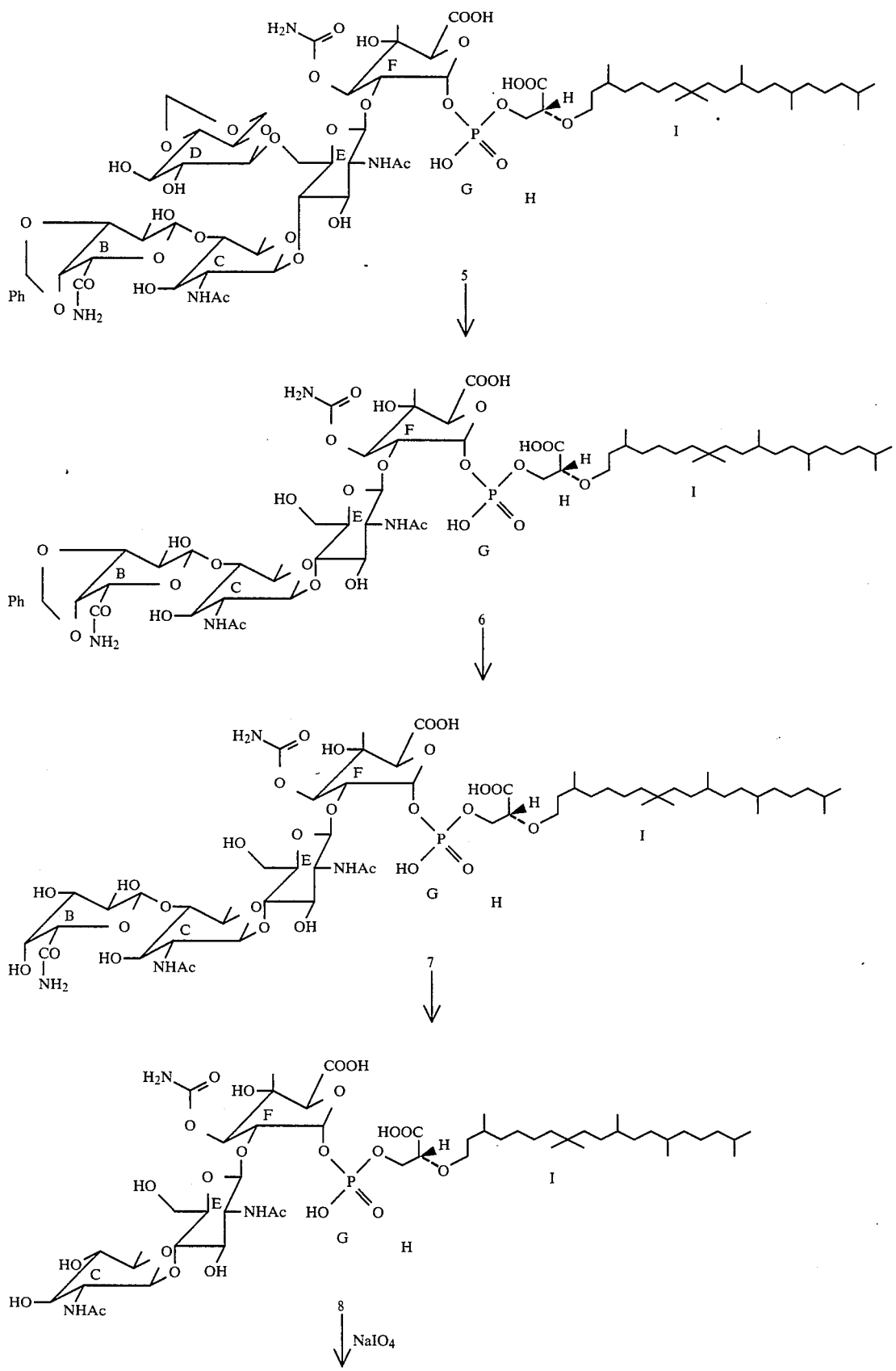

-continued

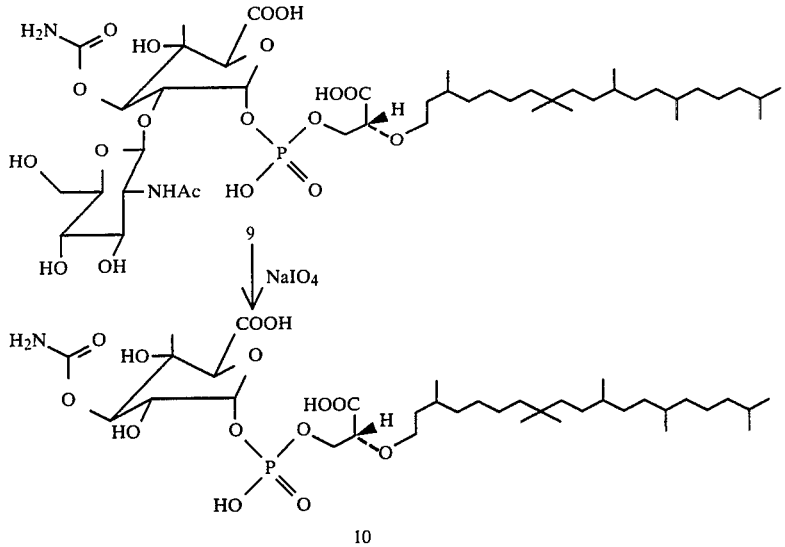

Compared with moenomycin A, the compounds 7 and 8, which are already described in P 33 01 430.2, and the compounds 9 and 10 according to the invention have improved stability and they have antibiotic activity, as is clear from the table below:

TABLE 1

| Antimicrobial activity (minimum inhibitory concentration in μg/ml) | | | | |
|---|---|---|---|---|
| Test organism | 7 | 8 | 9 | 10 |
| Staph. aureus SG 511 | 3.1 | 6.2 | 12.5 | — |
| Staph. aureus SG 503 | 3.1 | 12.5 | 12.5 | — |
| Strept. pyogenes 77 A | 0.8 | 1.6 | 1.6 | 3.1 |

The steps mentioned in the description are illustrated by the examples which follow:

EXAMPLE 1

Variant (a)

14.6 g of moenomycin A (1) and 4.5 g of Pd/C (10% Pd; 4.2 mmol) in 350 ml of methanol were stirred under hydrogen (180 bar) at 45° C. for 96 h. After decantation off from the catalyst, the latter was washed three times with methanol, and the solutions were combined and evaporated to dryness in vacuo at 35° C. Yield of decahydromoenomycin (2) 14 g (96%).

Variant (b)

13.09 g of moenomycin A (1, contaminated with delipidomoenomycin) and 3.53 g of PtO₂ in 1.3 liters of methanol, with the addition of 43 ml of acetic acid, were stirred at room temperature and under hydrogen at atmospheric pressure for 48 h. After decantation off from the catalyst, the latter was washed four times with methanol, and the solutions were applied to 220 g of HP-20. Elution was carried out with 2 liters of water, 1 liter of methanol/water 25/75, 1 liter of methanol/water 50/50 and 3 liters of methanol. The methanol fraction was evaporated to dryness and provided 8.04 g (61%) of decahydromoenomycin (2).

26.6 g (80.8 mmol) of $K_3Fe(CN)_6$ in 30 ml of water and 16.72 g (121 mmol) of $K_2CO_3$ in 30 ml of water were added, with stirring at 0° C., to 11.67 g (7.4 mmol) of 2 in 300 ml of water under argon. The temperature was increased to room temperature within 0.5 h, and the mixture was stirred for a further 1.5 h. The salts were removed by reverse phase chromatography (220 g of HP-20, mobile phase: 1.5 liters of water and 2.2 liters of methanol). Evaporation of the methanol solution provided 9.7 g of 3 (88%).

EXAMPLE 2

1.06 g (0.72 mmol) of 3, dissolved in 3 ml of dry DMSO, were added to a solution of 1.34 g (9.9 mmol) of anhydrous zinc chloride in 3 ml (28 mmol) of benzaldehyde at 90° C. under argon, and the mixture was stirred at 90°–95° C. for 52 h. The dark-brown reaction solution was prepurified by reverse phase chromatography (70 g of HP-20, mobile phase 200 ml of water, 150 ml of methanol/water 1:1, 200 ml of methanol/water 6:4, 100 ml of methanol/water 7:3 and about 1,000 ml of methanol).

1,416 mg of the freeze-dried, dark yellow methanol eluate were absorbed on 5 g of silica gel and chromatographed on 280 g of "Merck" silica gel (column type C) using the mobile phase chloroform/methanol/water 10:6:1 (fraction volume about 12 ml).

Fractions 37–66, which contained 5, were again chromatographed under the same conditions. The total yield of 5 was 92 mg (8%).

EXAMPLE 3

200 mg (0.12 mmol) of 5 were added, within 45 min, to 1,200 μl of a solution of 200 mg (0.93 mmol) of $NaIO_4$, 260 mg of sodium acetate.3H₂O and about 2.4 ml of 50% acetic acid, and the mixture was stirred at 38°–40° C., with exclusion of light, for 5 h. An orange-colored precipitate formed during the reaction. To separate off the salts, the reaction mixture was applied to a HP-20 reverse phase column and eluted first with 70 ml of water and then with about 400 ml of methanol. After freeze-drying, 170 mg (85%) of a non-polar product ($R_f$ value 0.33 in chloroform/methanol/water 18:11:2.7) were obtained.

95 mg (0.063 mmol) of this oxidation product were added to 240 μl of a solution of 470 μl (6.2 mmol) of N,N-dimethylhydrazine, 1.4 ml of isopropyl alcohol and about 2.8 ml of 2N $H_2SO_4$ (pH of the solution: 4.0), and the mixture was stirred at room temperature for 2.5 h and at 80°–90° C. for 1 hr. 5 ml of water were added to the reaction mixture and it was then freeze-dried. After absorption on about 0.5 g of "Merck" silica gel, chromatography was carried out on 60 g of silica gel (column type B) using the mobile phase chloroform/methanol/water 10:6:1. 35 mg (43%) of 6 were obtained ($R_f$ value 0.3 in chloroform/methanol/water 18:11:2.7).

EXAMPLE 4

180 mg (0.126 mmol) of 6 were dissolved in 0.5 ml of methanol and 4 ml of acetic acid and, after addition of 200 mg of Pd/C (10%), were hydrogenated under hydrogen at room temperature for 44 h. By thin-layer chromatography (chloroform/methanol/water 18:11:2.7), the reaction took place virtually uniformly. After washing the catalyst several times with methanol, the solution was concentrated and freeze-dried. 186.4 mg (100%) of the product 7 ($R_f$ value 0.1 in chloroform/methanol/water 18:11:2.7) were obtained.

EXAMPLE 5

300 $\mu$l of a solution composed of 200 mg (0.93 mmol) of $NaIO_4$, 260 mg of sodium acetate.$3H_2O$ and 2.4 ml of 50% acetic acid were added to 165 mg (0.12 mmol) of 7 dissolved in 0.6 ml of water, and the mixture was stirred at 25° C. for 2 h. After 2 h, 6 h, 19 h, 21 h, 25 h and 30 h, 150 $\mu$l, 190 $\mu$l, 150 $\mu$l, 100 $\mu$l, 200 $\mu$l and 300 ul respectively of the solution containing $NaIO_4$ were added, and the temperature was increased to 30° C. after 1G.5 h, and to 40° C. after 25 h. After a reaction time of 44 h, sodium metaperiodate and sodium acetate were removed on a HP-20 reverse phase column. Elution with about 500 ml of methanol provided, after evaporation, 122 mg (74%) of a mixed product.

260 $\mu$l of a solution composed of 470 $\mu$l of N,N-dimethylhydrazine, 1.4 ml of isopropyl alcohol and 2.5 ml of 2N $H_2SO_4$ (pH of the solution: 4.0-4.5) were added to a suspensibn of 122 mg of this mixed product in 700 $\mu$l of isopropyl alcohol, and the mixture was stirred at 50° C. for 1 h and at 80°-85° C. for 1 h. After absorption on 1 g of silica gel, chromatography was carried out on a 60 g of "Merck" silica gel (column type B) using the mobile phase chloroform/methanol/water 18:11:2.7, and 66 mg (45%) of substance 8 ($R_f$ value 0.21 in chloroform/methanol/water 18:11:2.7) were obtained.

EXAMPLE 6

1.0 g (0.7 mmol) of solid 3 was added in portions to a solution of 1.0 g (4.7 mmol) of $NaIO_4$ and 1.3 g of sodium acetate.$3H_2O$ in 12 ml of 50% acetic acid. The mixture was stirred, with exclusion of light, at 40° C. for 2 h. The brownish colored reaction mixture was then purified by reverse phase chromatography (40 g of HP-20; mobile phase: 600 ml of water and 600 ml of methanol). After concentration and freeze-drying of the methanol solution, 830 mg of oxidation products were obtained. 687 mg of this mixture were added in portions to 3 ml of a solution of 940 $\mu$l of N,N-dimethylhydrazine and 2.8 ml of 2-propanol in 6.4 ml of 2N $H_2SO_4$ (pH: 4.5). The mixture was stirred at 85° C. for 3 h. After cooling, purification was carried out by reverse phase chromatography (40 g of HP-20; mobile phase: 600 ml of water and 600 ml of methanol). The methanol solution was evaporated and freeze-dried. Column chromatography twice on "Merck" silica gel (column B, mobile phase: chloroform/methanol/water 10:6:1) provided 311 mg (47%) of 8.

EXAMPLE 7

2.35 g (2.0 mmol) of solid 8 were added in portions to a solution of 1.84 g (8.6 mmol) of $NaIO_4$ and 2.41 g (17.7 mmol) of NaOAc.$3H_2O$ in 21 ml of 50% acetic acid. The mixture was stirred at room temperature, with exclusion of light, for 2 hours. The inorganic salts were removed by reverse phase chromatography (50 g of HP-20; first 700 ml of water and then 1.5 liters of methanol). Concentration and freeze-drying of the methanol solution provided 1.76 g of pale yellow oxidation product.

1.76 g of this substance were added in portions to 6 ml of a solution of 940 $\mu$l of N,N-dimethylhydrazine and 2.8 ml of 2-propanol in 6.4 ml of 2N $H_2SO_4$ (pH 4.5). The mixture was stirred at 80°-85° C. for 3 h, and after cooling the dark-brown solution, it was applied to a HP-20 column. The salts were eluted with 600 ml of water, and the products were eluted with 1.2 liters of methanol. Concentration and freeze-drying of the latter phase provided 1.48 g of crude product.

Preparative layer chromatography on 75 g of silica gel (Woelm 63–100$\mu$, mobile phase chloroform/methanol/water 10:6:1) provided 1.02 g (52%) of 9.

Two subsequent separations on silica gel columns using the same mobile phase provided 69.8 mg of analytically pure substance from 210 mg of product.

$^{13}C$ NMR spectrum: FIG. 1

EXAMPLE 8

940 mg (0.96 mmol) of 9 were stirred with a solution of 974 mg (4.6 mmol) of $NaIO_4$ and 1.28 g of NaOAc.$3H_2O$ in 11 ml of 50% acetic acid at room temperature in the dark for 2 hours. Working up over a reverse phase column (25 g of HP-20, mobile phase 400 ml of water and then 1.5 liters of methanol) provided, after concentration and freeze-drying of the methanol solution, 648 mg of yellow substance.

620 mg of this product were stirred with 4 ml of a solution of 940 $\mu$l of N,N-dimethylhydrazine and 2.8 ml of 2-propanol in 6.4 ml of 2N $H_2SO_4$ (pH 4.5), first at room temperature for 1 hour and then at 80°-85° C. for 2 hours. After cooling and application to a HP-20 column (25 g), the salts were eluted with 300 ml of water and the products were eluted with 1.5 liters of methanol. 0.54 g of pale brown product was obtained from the methanol phase after freeze-drying.

Preparative layer chromatography on silica gel (Merck, mobile phase chloroform/methanol/water 10:6:1) provided 138 mg of 10 (19%), together with 296 mg of 9 (31%).

Two subsequent separations on 8 columns using the mobile phase chloroform/methanol/water 17.5:7.5:1 provided 60.3 mg of analytically pure substance from 138 mg of 10.

Figure 2:
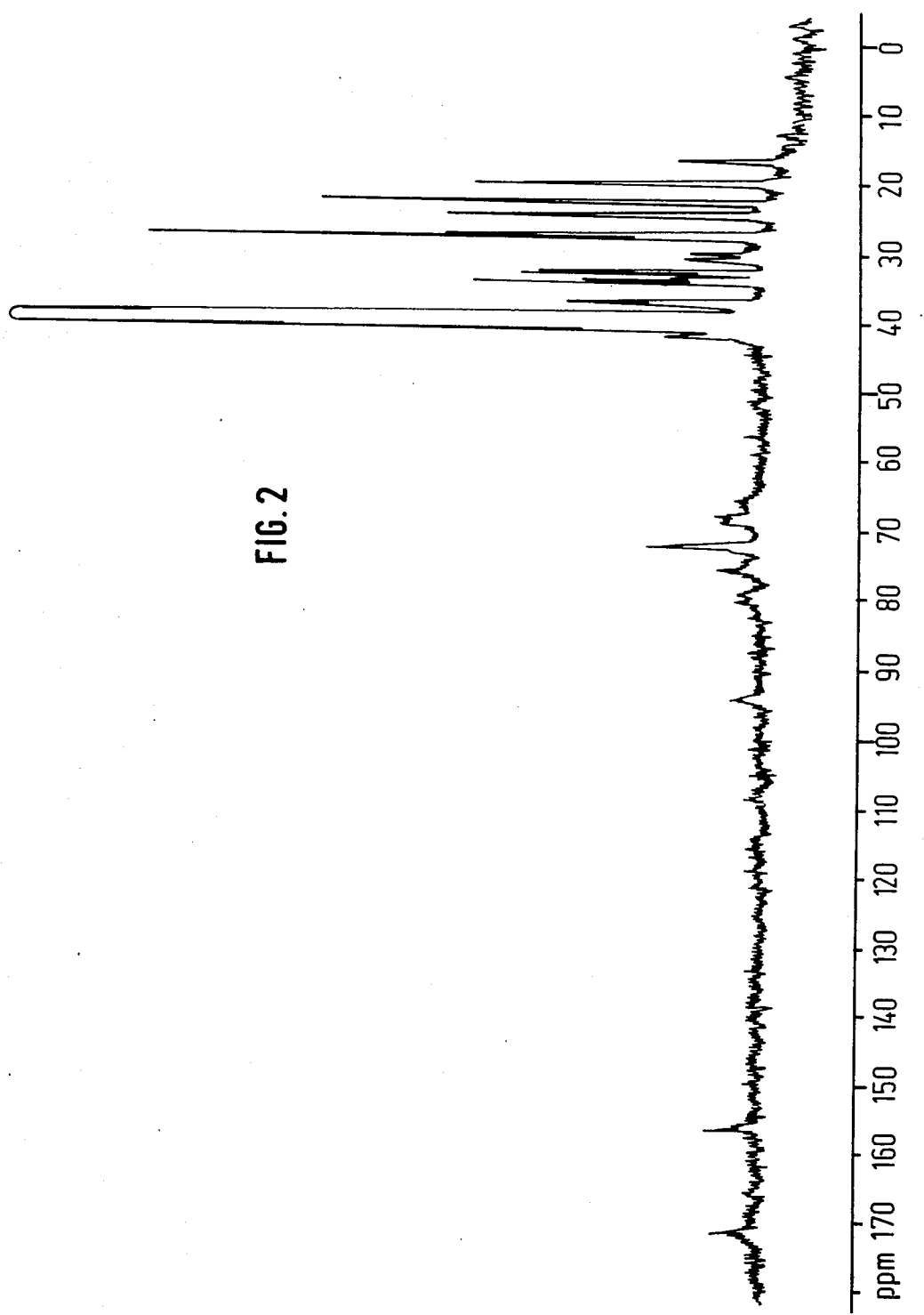

$^{13}C$ NMR spectrum: FIG. 2

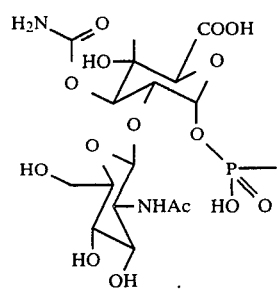
2. A compound of the formula
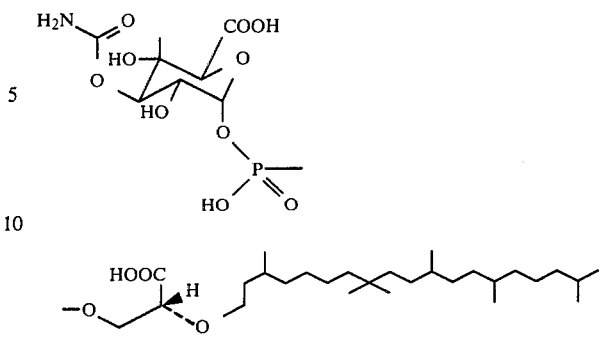
3. A method of treating microbial diseases comprising the administration to a host of a therapeutically effective amount of the compound of claim 1.
4. A method of treating microbial diseases comprising the administration to a host of a therapeutically effective amount of the compound of claim 2.
* * * * *
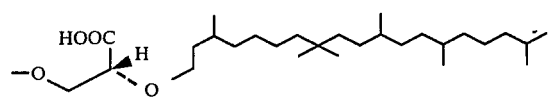

We claim:

1. A compound of the formula